United States Patent [19]

Crugnola et al.

[11] Patent Number: 4,797,411
[45] Date of Patent: Jan. 10, 1989

[54] CYCLOALKYL-SUBSTITUTED 4-PYRIDYL DERIVATIVES AND USE AS AROMATASE INHIBITORS

[75] Inventors: Angelo Crugnola, Varese; Enrico di Salle; Paolo Lombardi, both of Milan, all of Italy

[73] Assignee: Farmitalia Carlo Erba S.p.A., Milan, Italy

[21] Appl. No.: 72,678

[22] Filed: Jul. 13, 1987

[30] Foreign Application Priority Data

Jul. 18, 1986 [GB] United Kingdom ............... 8617596
Nov. 24, 1986 [GB] United Kingdom ............... 8628029

[51] Int. Cl.$^4$ .................. A61K 31/44; C07D 213/26; C07D 213/28; C07D 213/24
[52] U.S. Cl. .................................. 514/357; 514/277; 546/329; 546/334; 546/337; 546/339; 546/340; 546/342; 546/348
[58] Field of Search ............. 546/334, 337, 329, 340, 546/342, 339, 348; 514/277, 357

[56] References Cited

U.S. PATENT DOCUMENTS 4,410,697 10/1983 Torok et al. ............... 546/337
4,617,307 10/1986 Browne .................... 514/357

OTHER PUBLICATIONS

Kellis et al., Endocrinology, vol. 114, No. 6, pp. 2128–2127.
Wells et al., Ann. Surg., May 1978, pp. 475–484.
Harris et al., Eur. J. Cancel Clin Oncol., vol. 19, No. 1, pp. 11–17 (1983).
Breast Cancel Research & Treatment, 2, pp. 375–383 (1982).
Foster et al., J. Med. Chem. 1985, 28, pp. 200–204.
Asbury et al., Cancer, 47:1954–1958 (1981).
Smith et al., The Lancet. 9/23/78, pp. 646–649.
Cash et al., J. Chin. Endocrinology 67;27, pp. 1239–1248.

J. Chin Endocrinology-Metabolism, vol. 27, No. 7, pp. 1684–1695 (1967).
Brodie; A., Pharm of Aromatase Inhibitors, pp. 255–270.
Manni et al., Clinical Uses of Aromatase Inhibitors, pp. 271–287.
Mins, Oct. 1984.
Vidal Dictionnaire 1985, pp. 1050–1051.
Merck Index, 10th Ed., 443–444.

*Primary Examiner*—Mary C. Lee
*Assistant Examiner*—J. Richter
*Attorney, Agent, or Firm*—Armstrong, Nikaido, Marmelstein & Kubovcik

[57] ABSTRACT

The invention relates to cycloalkyl-substituted 4-pyridyl derivatives of formula (I)

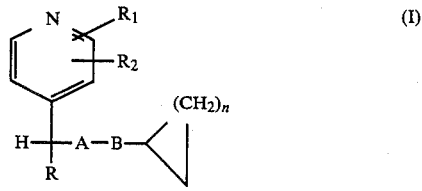

wherein
R is $C_1$–$C_4$ alkyl;
each of $R_1$ and $R_2$ is, independently, hydrogen or $C_1$–$C_4$ alkyl;
n is an integer of 1 to 5; and either
(a) A is >C=O and B is —O—, —NH— or —$CH_2$—; or
(b) A is —$CH_2$—and B is —O—, —NH—, —$CH_2$— or >C=O; or
(c) A is —O— and B is >C=O or —$CH_2$—; or
(d) A is —NH— and B is >C=O or —$CH_2$—,
and their pharmaceutically acceptable salts.

The compounds of the invention show aromatase inhibiting activity and can be useful, e.g., in treating hormone-dependent tumors and prostatic hyperplasia.

17 Claims, No Drawings

CYCLOALKYL-SUBSTITUTED 4-PYRIDYL DERIVATIVES AND USE AS AROMATASE INHIBITORS

The present invention relates to cycloalkyl-substituted 4-pyridyl derivatives, to a process for their preparation, to pharmaceutical compositions containing them and to the use of said compounds as inhibitors of the biosynthesis of estrogens, particularly as aromatase inhibitors.

Basic and clinical data indicate that estrogens are the hormones involved in the pathogenic cellular changes associated with the growth of some hormone-dependent cancers, such as breast, pancreatic, endometrial and ovarian carcinoma.

Estrogens are also involved in the pathogenesis of benign prostatic hyperplasia. It has been envisaged that an effective inhibition of the biosynthesis of estrogens, better if resulting from compounds able to neutralize the activity of the enzyme aromatase which performs the aromatisation of the steroid ring A, may have useful application for controlling the amount of circulating estrogens, and estrogen-dependent tumors.

Non-steroidal known substances which have been reported to be endowed with a more or less selective aromatase-inhibiting action are, for example, aminoglutethimide [Ann. Surg. 187, 475 (1978); Lancet, 2, 646 (1978)]; 4-cyclohexylaniline [Endocrinology, 114, 2128 (1984)], and 4-pyridyl-3-ethyl-2,6-piperidinedione [J. Med. Chem., 28, 200 (1985)].

The invention provides a new group of non-steroidal substances having aromatase-inhibiting properties, which are cycloalkyl-substituted 4-pyridyl derivatives having the general formula (I)

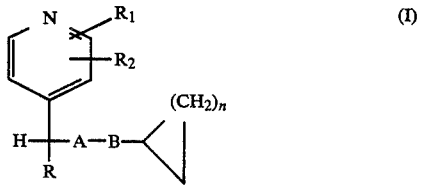

wherein
R is $C_1$–$C_4$ alkyl;
each of $R_1$ and $R_2$ is, independently, hydrogen or $C_1$–$C_4$ alkyl;
n is an integer of 1 to 5; and either
(a) A is $>C=O$ and B is —O—, —NH— or —CH$_2$—; or
(b) A is —CH$_2$— and B is —O—, —NH—, —CH$_2$— or $>C=O$; or
(c) A is —O— and B is $>C=O$ or —CH$_2$—; or
(d) A is —NH— and B is $>C=O$ or —CH$_2$—.

Also the pharmaceutically acceptable salts of the compounds of formula (I) are included within the scope of the invention. The said salts are the salts with pharmaceutically acceptable acids, both inorganic acids, such as, e.g., hydrochloric and sulfuric, and organic such as, e.g., citric, tartaric, maleic, malic, succinic, methanesulfonic and ethanesulfonic.

In this specification the terms "pharmaceutical" and "pharmaceutically" are meant to refer not only to the pharmaceutical field but also to the veterinary field.

All the possible isomers of formula (I) are included within the scope of the invention, both separately and in mixture.

Thus, for example, for each compound of formula (I) two distinct optical isomers, i.e., enantiomers, may exist according to the configuration of the chiral carbon atom carrying the R substituent. The formula (I) is meant to cover both the enantiomers, either separately or in mixture.

Preferred enantiomers according to the invention are those represented by the formula (Ia)

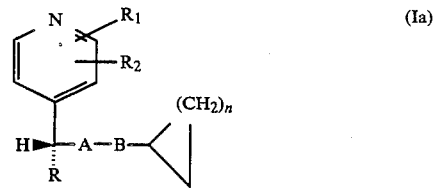

wherein
R, $R_1$, $R_2$, n, A and B are as defined above.

In the above formulae a $C_1$–$C_4$ alkyl group is, preferably, methyl or ethyl, especially methyl.

Preferably, either $R_1$ and $R_2$ are both hydrogen or both methyl groups, or one of them is hydrogen and the other is methyl. Preferred values for n are 3 and 4, in particular 4. Preferred salts are the hydrochlorides.

A particularly preferred class of compounds according to the invention are the compounds of formula (I) wherein R is $C_1$–$C_4$ alkyl; each of $R_1$ and $R_2$ is, independently, hydrogen or $C_1$–$C_4$ alkyl; n is an integer of 1 to 5; A is $>C=O$ or —CH$_2$—, and B is, independently, —O—, —NH— or —CH$_2$—, and the pharmaceutically acceptable salts thereof.

In the above preferred class preferred enantiomers are those represented by the formula (Ia); preferred values of R are methyl and ethyl, in particular methyl; preferably $R_1$ and $R_2$ are both hydrogen or both methyl groups, or one of them is hydrogen and the other is methyl; and, preferably, n is 3 or 4, in particular 4.

Examples of specific compounds under this invention are:
cyclohexyl 2-(4'-pyridyl)propionate;
cyclohexyl 2-(2'-methylpyrid-4'-yl)propionate;
cyclohexyl 2-(3'-methylpyrid-4'-yl)propionate;
cyclohexyl 2-(2',6'-dimethylpyrid-4'-yl)propionate;
cyclohexyl 2-(2',5'-dimethylpyrid-4'-yl)propionate;
cyclohexyl 2-(2',3'-dimethylpyrid-4'-yl)propionate;
cyclohexyl 2-(3',5'-dimethylpyrid-4'-yl)propionate;
N-cyclohexyl-2-(4'-pyridyl)propanamide;
N-cyclohexyl-2-(2'-methylpyrid-4'-yl)propanamide;
N-cyclohexyl-2-(3'-methylpyrid-4'-yl)propanamide;
N-cyclohexyl-2-(2',6'-dimethylpyrid-4'-yl)propanamide;
N-cyclohexyl-2-(2',5'-dimethylpyrid-4'-yl)propanamide;
N-cyclohexyl-2-(2',3'-dimethylpyrid-4'-yl)propanamide;
N-cyclohexyl-2-(3',5'-dimethylpyrid-4'-yl)propanamide;
2-(4'-pyridyl)propylcyclohexyl ether;
2-(2'-methylpyrid-4'-yl)propylcyclohexyl ether;
2-(3'-methylpyrid-4'-yl)propylcyclohexyl ether;
2-(2',6'-dimethylpyrid-4'-yl)propylcyclohexyl ether;
2-(2',5'-dimethylpyrid-4'-yl)propylcyclohexyl ether;
2-(2',3'-dimethylpyrid-4'-yl)propylcyclohexyl ether;

2-(3',5'-dimethylpyrid-4'-yl)propylcyclohexyl ether;
N-cyclohexyl-2-(4'-pyridyl)propylamine;
N-cyclohexyl-2-(2'-methylpyrid-4'-yl)propylamine;
N-cyclohexyl-2-(3'-methylpyrid-4'-yl)propylamine;
N-cyclohexyl-2-(2',6'-dimethylpyrid-4'-yl)propylamine;
N-cyclohexyl-2-(2',5'-dimethylpyrid-4'-yl)propylamine;
N-cyclohexyl-2-(2',3'-dimethylpyrid-4'-yl)propylamine;
N-cyclohexyl-2-(3',5'-dimethylpyrid-4'-yl)propylamine;
1-cyclohexyl-3-(4'-pyridyl)-2-butanone;
1-cyclohexyl-3-(2'-methylpyrid-4'-yl)-2-butanone;
1-cyclohexyl-3-(3'-methylpyrid-4'-yl)-2-butanone;
1-cyclohexyl-3-(2',6'-dimethylpyrid-4'-yl)-2-butanone;
1-cyclohexyl-3-(2',5'-dimethylpyrid-4'-yl)-2-butanone;
1-cyclohexyl-3-(2',3'-dimethylpyrid-4'-yl)-2-butanone;
1-cyclohexyl-3-(3',5'-dimethylpyrid-4'-yl)-2-butanone;
1-cyclohexyl-3-(4'-pyridyl)butane;
1-cyclohexyl-3-(2'-methylpyrid-4'-yl)butane;
1-cyclohexyl-3-(3'-methylpyrid-4'-yl)butane;
1-cyclohexyl-3-(2',6'-dimethylpyrid-4'-yl)butane;
1-cyclohexyl-3-(2',5'-dimethylpyrid-4'-yl)butane;
1-cyclohexyl-3-(2',3'-dimethylpyrid-4'-yl)butane;
1-cyclohexyl-3-(3',5'-dimethylpyrid-4'-yl)butane;
1-(4'-pyridyl)ethyl cyclohexanecarboxylate;
1-(2'-methylpyrid-4'-yl)ethyl cyclohexanecarboxylate;
1-(3'-methylpyrid-4'-yl)ethyl cyclohexanecarboxylate;
1-(2',6'-dimethylpyrid-4'-yl)ethyl cyclohexanecarboxylate;
1-(2',5'-dimethylpyrid-4'-yl)ethyl cyclohexanecarboxylate;
1-(2',3'-dimethylpyrid-4'-yl)ethyl cyclohexanecarboxylate;
1-(3',5'-dimethylpyrid-4'-yl)ethyl cyclohexanecarboxylate;
1-(4'-pyridyl)ethyl cyclohexylmethyl ether;
1-(2'-methylpyrid-4'-yl)ethyl cyclohexylmethyl ether;
1-(3'-methylpyrid-4'-yl)ethyl cyclohexylmethyl ether;
1-(2',6'-dimethylpyrid-4'-yl)ethyl cyclohexylmethyl ether;
1-(2',5'-dimethylpyrid-4'-yl)ethyl cyclohexylmethyl ether;
1-(2',3'-dimethylpyrid-4'-yl)ethyl cyclohexylmethyl ether;
1-(3',5'-dimethylpyrid-4'-yl)ethyl cyclohexylmethyl ether;
N-[1-(4'-pyridyl)ethyl]cyclohexancarboxyamide;
N-[1-(2'-methylpyrid-4'-yl)ethyl]cyclohexanecarboxyamide;
N-[1-(3'-methylpyrid-4'-yl)ethyl]cyclohexanecarboxyamide;
N-[1-(2',6'-dimethylpyrid-4'-yl)ethyl]cyclohexanecarboxyamide;
N-[1-(2',5'-dimethylpyrid-4'-yl)ethyl]cyclohexanecarboxyamide;
N-[1-(2',3'-dimethylpyrid-4'-yl)ethyl]cyclohexanecarboxyamide;
N-[1-(3',5'-dimethylpyrid-4'-yl)ethyl]cyclohexanecarboxyamide;
N-[1-(4'-pyridyl)ethyl]cyclohexylmethylamine;
N-[1-(2'-methylpyrid-4'-yl)ethyl]cyclohexylmethylamine;
N-[1-(3'-methylpyrid-4'-yl)ethyl]cyclohexylmethylamine;
N-[1-(2',6'-dimethylpyrid-4'-yl)ethyl]cyclohexylmethylamine;
N-[1-(2',5'-dimethylpyrid-4'-yl)ethyl]cyclohexylmethylamine;
N-[1-(2',3'-dimethylpyrid-4'-yl)ethyl]cyclohexylmethylamine;
N-[1-(3',5'-dimethylpyrid-4'-yl)ethyl]cyclohexylmethylamine;
2-(4'-pyridyl)propylcyclohexylketone;
2-(2'-methylpyrid-4'-yl)propylcyclohexylketone;
2-(3'-methylpyrid-4'-yl)propylcyclohexylketone;
2-(2',6'-dimethylpyrid-4'-yl)propylcyclohexylketone;
2-(2',5'-dimethylpyrid-4'-yl)propylcyclohexylketone;
2-(2',3'-dimethylpyrid-4'-yl)propylcyclohexylketone;
2-(3',5'-dimethylpyrid-4'-yl)propylcyclohexylketone,
and the pharmaceutically acceptable salts thereof.

A group of particularly preferred specific compounds of the invention are the compounds selected from the group consisting of:
cyclohexyl 2-(4'-pyridyl)propionate;
cyclohexyl 2-(2'-methylpyrid-4'-yl)propionate;
cyclohexyl 2-(3'-methylpyrid-4'-yl)propionate;
cyclohexyl 2-(2',6'-dimethylpyrid-4'-yl)propionate;
cyclohexyl 2-(2',5'-dimethylpyrid-4'-yl)propionate;
cyclohexyl 2-(2',3'-dimethylpyrid-4'-yl)propionate;
cyclohexyl 2-(3',5'-dimethylpyrid-4'-yl)propionate;
N-cyclohexyl-2-(4'-pyridyl)propanamide;
N-cyclohexyl-2-(2'-methylpyrid-4'-yl)propanamide;
N-cyclohexyl-2-(3'-methylpyrid-4'-yl)propanamide;
N-cyclohexyl-2-(2',6'-dimethylpyrid-4'-yl)propanamide;
N-cyclohexyl-2-(2',5'-dimethylpyrid-4'-yl)propanamide;
N-cyclohexyl-2-(2',3'-dimethylpyrid-4'-yl)propanamide;
N-cyclohexyl-2-(3',5'-dimethylpyrid-4'-yl)propanamide;
2-(4'-pyridyl)propylcyclohexyl ether;
2-(2'-methylpyrid-4'-yl)propylcyclohexyl ether;
2-(3'-methylpyrid-4'-yl)propylcyclohexyl ether;
2-(2',6'-dimethylpyrid-4'-yl)propylcyclohexyl ether;
2-(2',5'-dimethylpyrid-4'-yl)propylcyclohexyl ether;
2-(2',3'-dimethylpyrid-4'-yl)propylcyclohexyl ether;
2-(3',5'-dimethylpyrid-4'-yl)propylcyclohexyl ether;
N-cyclohexyl-2-(4'-pyridyl)propylamine;
N-cyclohexyl-2-(2'-methylpyrid-4'-yl)propylamine;
N-cyclohexyl-2-(3'-methylpyrid-4'-yl)propylamine;
N-cyclohexyl-2-(2',6'-dimethylpyrid-4'-yl)propylamine;
N-cyclohexyl-2-(2',5'-dimethylpyrid-4'-yl)propylamine;
N-cyclohexyl-2-(2',3'-dimethylpyrid-4'-yl)propylamine;
N-cyclohexyl-2-(3',5'-dimethylpyrid-4'-yl)propylamine;
1-cyclohexyl-3-(4'-pyridyl)-2-butanone;
1-cyclohexyl-3-(2'-methylpyrid-4'-yl)-2-butanone;
1-cyclohexyl-3-(3'-methylpyrid-4'-yl)-2-butanone;
1-cyclohexyl-3-(2',6'-dimethylpyrid-4'-yl)-2-butanone;
1-cyclohexyl-3-(2',5'-dimethylpyrid-4'-yl)-2-butanone;
1-cyclohexyl-3-(2',3'-dimethylpyrid-4'-yl)-2-butanone;
1-cyclohexyl-3-(3',5'-dimethylpyrid-4'-yl)-2-butanone;
1-cyclohexyl-3-(4'-pyridyl)butane;
1-cyclohexyl-3-(2'-methylpyrid-4'-yl)butane;
1-cyclohexyl-3-(3'-methylpyrid-4'-yl)butane;
1-cyclohexyl-3-(2',6'-dimethylpyrid-4'-yl)butane;
1-cyclohexyl-3-(2',5'-dimethylpyrid-4'-yl)butane;
1-cyclohexyl-3-(2',3'-dimethylpyrid-4'-yl)butane;
1-cyclohexyl-3-(3',5'-dimethylpyrid-4'-yl)butane;
and the pharmaceutically acceptable salts thereof.

The compounds of formula (I) may be prepared by a process comprising
(1) introducing a group R, by alkylation, into a compound of formula (II)

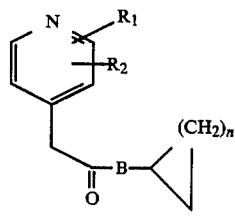

wherein
B is —O—, —NH— or —CH$_2$— and R$_1$,R$_2$ and n are as defined above, so obtaining a compound of formula (I) wherein R,R$_1$,R$_2$ and n are defined as above, A is >C=O and B is —O—, —NH— or —CH$_2$—; or (2) reacting a compound of formula (III)

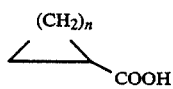

wherein n is as defined above, or a reactive derivative thereof, with a compound of formula (IV)

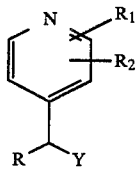

wherein
R,R$_1$ and R$_2$ are as defined above and Y is —OH, —NH$_2$ or a group —CH$_2$—M—X wherein M is a metal and X is halogen, so obtaining a compound of formula (I) wherein R,R$_1$,R$_2$ and n are as defined above, A is —O—, —NH— or —CH$_2$ and B is >C=O, or (3) reducing a compound of formula (I) wherein R,R$_1$,R$_2$ and n are as defined above and either (i) A is >C=O and B is —O— or NH or (ii) A is —O— or —NH— and B is >C=O, so obtaining a corresponding compound of formula (I) wherein either (i') A is —CH$_2$— and B is —O— or NH or (ii') A is —O— or NH and B is —CH$_2$—; or (4) deoxygenating a compound of formula (I) wherein R, R$_1$, R$_2$ and n are as defined above and either A is >C=O and B is —CH$_2$— or A is —CH$_2$— and B is >C=O, so obtaining a corresponding compound of formula (I) wherein A and B are both —CH$_2$—; and, if desired, salifying a compound of formula (I) or obtaining a free compound of formula (I) from a salt thereof and/or, if desired, separating a mixture of isomers of formula (I) into the single isomers.

The introduction of the group R into the compound of formula (II) is preferably performed using an alkylating agent of formula R—X, wherein R and X are as defined above, the halogen X being, preferably, bromine or iodine; the reaction is preferably carried out in an inert organic solvent such as, for instance tetrahydrofuran, diethyl ether, dimethoxyethane, dioxane and similar, in the presence of a strong base such as, for instance, sodium or potassium hydride, n-butyl lithium, lithium diisopropylamide and similar, at a temperature ranging between about −78° C. and about 50° C.

A reactive derivative of an acid of formula (III) may be, e.g., an acyl halide, in particular the chloride of the acid, or the anhydride thereof, or the imidazolide thereof.

The reaction of a compound of formula (III), or a reactive derivative thereof, with a compound of formula (IV) wherein Y is —OH or —NH$_2$ may be performed following usual procedures described in organic chemistry for esterification or, respectively, amidation reactions. For example the compound of formula (III) or a reactive derivative thereof, such as, for instance, an halide, e.g. the chloride, or the imidazolide thereof, may be reacted with the desired alcohol (Y=—OH) or, respectively, amine (Y=—NH$_2$) of formula (IV) operating, e.g., at room temperature in an inert, preferably anhydrous, organic solvent, such as, for instance, tetrahydrofuran or benzene, and isolating the formed ester or, respectively, amide of formula (I) in a conventional way.

When in the compound of formula (IV) Y is a group —CH$_2$—M—X, the symbol M represents a metal, preferably Mg, suitable to give a Grignard reagent, and the halogen X is, preferably, iodine, bromine or chlorine.

The reaction of a compound of formula (III) or a reactive derivative thereof, with a compound of formula (IV), wherein Y is a group —CH$_2$—M—X as defined above, may be carried out in the usual conditions described in the organic chemistry for the Grignard reactions, preferably operating in an inert and anhydrous organic solvent, e.g. diethyl ether or tetrahydrofuran, at a very low temperature, e.g. around the range between −60° C. and −40° C.

The reduction of a compound of formula (I) wherein either (i) A is >C=O and B is —O— or —NH— or (ii) A is —O— or —NH— and B is >C=O is carried out by means of a suitable reducing agent such as, for instance, a hydride, e.g. B$_2$H$_6$, or a mixed hydride, e.g. LiAlH$_4$, operating in an inert solvent such as, e.g. tetrahydrofuran, dioxane, diglyme and similar solvents, preferably at a temperature ranging between about 40° C. and about 120° C. for a reaction time varying approximately in the range of 4–48 hours.

The deoxygenation of a compound of formula (I) wherein A is >C=O and B is —CH$_2$— or A is —CH$_2$— and B is >C=O is preferably carried out by transforming the carbonyl group into the corresponding 1,3-dithiolane according to general methods, and then reducing the latter derivative by the action of an alkali metal, such as, e.g., lithium, sodium or calcium, dissolving in liquid ammonia.

Alternatively, the 1,3-dithiolane derivative may be reduced by Raney-Nickel in an inert solvent, such as, e.g., ethanol, dioxane, acetone, at a temperature ranging between about 20° C. and about 80° C. for a reaction time of about 0.5–4 hours, or also by tributyl tin hydride in an inert aprotic solvent, preferably benzene, at a temperature ranging between about 60° C. and about 100° C., for a reaction time of about 1–3 hours. Optionally, the carbonyl group in the compound of formula (I) may be transformed into the corresponding tosylhydrazone by general methods and the derivative so obtained may be reduced by the action of hydrides, for instance with lithium aluminium hydride or bis(benzoyloxy)borane, operating in an inert, aprotic solvent such as, e.g., diethylether, dioxane, tetrahydrofuran, diglyme, chloroform or methylene chloride, at a temperature ranging between about 0° C. and around 40° C. and for reaction times of about 0.5–4 hours; or with sodium cyanoborohydride operating in a protic solvent such as, e.g., methanol, ethanol, or propanol, at temperature ranging between around 40° C. and around 100° C. for a reaction time of about 1-24 hours.

The optional salification of a compound of formula (I) and the preparation of a free compound of formula (I) from a salt thereof may be performed by conventional known methods. Standard procedures may be followed also for separating a mixture of isomers into the single isomers, in particular, for example, for separating a racemic mixture into the single enantiomers.

A compound of formula (II) wherein B is —O— or —NH— may be prepared reacting a compound of formula (V)

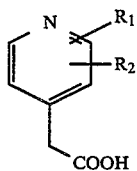

(V)

wherein $R_1$ and $R_2$ are as defined above, or, preferably, a reactive derivative thereof such as, for instance, a corresponding acyl halide e.g. chloride, or the anhydride thereof or the imidazolide thereof, with a compound of formula (VI) or, respectively, a compound of formula (VII)

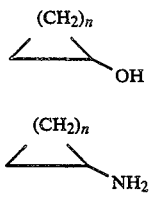

(VI)

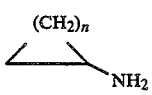

(VII)

wherein n is as defined above.

Usual procedures described in the organic chemistry for esterification and, respectively, amidation reactions may be followed, e.g. as indicated before for the analogous reaction between compounds (III) and compounds (IV) wherein Y is —OH or, respectively, —NH$_2$—.

A compound of formula (II) wherein B is —CH$_2$— may be prepared reacting a compound of formula (V) or, preferably, a reactive derivative thereof, e.g., of the kind previously indicated, with a compound of formula (VIII)

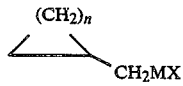

(VIII)

wherein n, M and X are as defined above. The reaction may be carried out in the usual conditions described in the organic chemistry for the Grignard reactions, e.g. as previously indicated for the analogous reaction between compounds (III) and compounds (IV) wherein Y is —CH$_2$—M—X.

The compounds having the formulae (III), (IV), (V), (VI), (VII), and (VIII) are commercially available compounds or known compounds which may be prepared by known methods from known compounds.

The compounds of the present invention are inhibitors of the biotransformation of androgens into estrogens, i.e., they are steroidal aromatase inhibitors.

The inhibition of aromatase activity by these compounds was demonstrated by employing the in vivo test in rats described by Brodie (A. M. H. Brodie et al. Steroids, 38, 693, 1981), slightly modified.

Adult female rats were twice treated subcutaneously with 100 I.U. pregnant mares' serum gonadotropin (PMSG) at 4 days' interval, in order to increase ovarian aromatase activity and, consequently, serum estradiol levels.

Four days after the second PMSG treatment, groups of 6 animals each were given the vehicle (0.5% methocel) or the aromatase inhibitor at 30 mg/Kg by the oral route.

Animals were killed by decapitation 6 hours later and sera were obtained and stored at $-20°$ C. for estradiol assay. Estradiol was assayed with commercially available radioimmunoassay kits, according to the manufacturer's instructions. Thus, for example, when the compound of the invention N-cyclohexyl-2-(4'-pyridyl)-propanamide was tested according to the procedure described above, a highly statistically significant ($p<0.01$) decrease in estrogen levels was found, as shown in the following table:

TABLE

Inhibition of rat ovarian aromatase in PMSG-pretreated rats.

| Compound | Dose mg/Kg os | Serum estradiol ng/ml (± S.E.) | % inhibition |
|---|---|---|---|
| Vehicle | — | 314 ± 48 | — |
| N—cyclohexyl-2--(4'-pyridyl)propanamide | 30 | 45 ± 2 | 86 |

By virtue of their ability to inhibit aromatase and, consequently, to reduce estrogen levels, the compounds of the invention can be useful in the treatment and prevention of various estrogen dependent diseases, such as, for instance, estrogen dependent tumors, e.g., breast, endometrial, ovarian and pancreatic cancers; gynecomastia; benign breast disease; endometriosis; polycystic ovarian disease; and precocious puberty.

Another application of the compounds of the invention may be in the therapeutic and/or prophylactic treatment of prostatic hyperplasia, a disease of the estrogen dependent stromal tissue.

The compounds of the invention can find also use for the treatment of male infertility associated with oligospermia and for female fertility control, by virtue of their ability to inhibit ovulation and egg nidation.

The compounds of the invention can also be useful in the veterinary field, in all the situations in which a decrease in estrogen synthesis is desirable.

The compounds of the invention can be administered in a variety of dosage forms, e.g., orally, in the form of tablets, capsules, sugar or film coated tablets, liquid solutions or suspensions, rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 400 mg pro dose, from 1 to 5 times daily.

As already said the invention includes pharmaceutical composition comprising a compound of the invention in association with a pharmaceutically acceptable excipient (which can be carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose, or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar coating, or film-coating processes.

The liquid dispersion for oral administration may be e.g. syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired a suitable amount of lidocaine hydrochloride.

The solutions for intravenous injections or infusions may contain as carrier, for example, sterile water or, preferably, they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

When the configuration is unspecified, the compounds are meant to be racemic compounds, i.e. racemates.

EXAMPLE 1

N-cyclohexyl-4-pyridylacetamide [II, B=NH, n=4]

To a stirred suspension of 4-pyridyl acetic acid hydrochloride (1.73 g, 10 mmole) in anhydrous tetrahydrofuran (10 ml), is added N,N'-carbonyldiimidazole (1.62 g, 10 mmole) at 25° C. After 2 hrs of additional stirring there is added cyclohexylamine (1.15 ml, 10 mmole) dissolved in tetrahydrofuran (15 ml) dropwise. The reaction mixture is stirred overnight, the solvent is evaporated in vacuo and the residue in taken up with water (25 ml) and ethyl acetate (50 ml).

The pH is adjusted by the addition of 1N NaOH aqueous solution (11 ml), the organic phase is separated and the aqueous phase extracted with ethyl acetate (2×50 ml).

The combined extracts (150 ml) are washed with water, brine, dried over sodium sulfate, filtered and evaporated in vacuo. The resulting residue is purified by crystallisation from hot water (50 ml) at 5°-10° C.

There are obtained 450 mg (21% yield) of the title compound, m.p.: 147°-8° C.

Elemental analysis: calculated % (found %): C 71.52 (71.45), H 8.31 (8.33), N 12.83 (12.87).

IR (CHCl$_3$, cm$^{-1}$): 3420, 1660, 1600, 1555.

In analogous fashion and starting from the appropriate precursor of formula (VI) or, respectively of formula (VII) the following compounds may be prepared:
N-cyclopentyl-4-pyridylacetamide;
N-cyclopropyl-4-pryidylacetamide;
Cyclohexyl 4-pryidylacetate;
Cyclopentyl 4-pyridylacetate; and
Cyclopropyl 4-pyridylacetate.

EXAMPLE 2

1-cyclohexyl-3-(4'-pyridyl)-2-propanone hydrochloride [II, B=—CH$_2$—, n=4]

To a stirred solution of cyclohexyl methyl magnesium iodide (prepared from 3.5 g of cyclohexyl methyl iodide and 0.350 g of magnesium turnings) in anhydrous diethyl ether (30 ml) cooled to −70° C. are added 10 mmole of the imidazoyl derivative of 4-pyridylacetic acid (prepared as described in the Example 1). After 4 hours of additional stirring at that temperature, the reaction mixture is allowed to reach room temperature naturally and it is carefully decomposed by the dropwise addition of a saturated ammonium chloride aqueous solution. The organic phase is separated and the aqueous phase is extracted with diethyl ether (2×50 ml). The combined extracts are washed with brine, dried over sodium sulfate, filtered and evaporated in vacuo. The resulting residue is dissolved in diethyl ether, precipitated with gaseous HCl and filtered. The resulting precipitate is purified by crystallization from ethanol-diethyl ether. There are obtained 930 mg (36% yield) of the title compound as hydrochloride, m.p. 122°-5° C.

Elemental analysis: Calculated % (found %) C 66.26 (65.70), H 7.94 (7.95), N 5.52 (5.43), Cl 13.97 (13.43).

IR (CHCl$_3$, cm$^{-1}$): 3080, 2700-1900, 1715, 1630.

In analogous fashion and starting from the appropriate precursors of formula (VIII), the following compounds may be prepared:
1-cyclopentyl-3-(4'-pyridyl)-2-propanone; and
1-cyclopropyl-3-(4'-pyridyl)-2-propanone.

EXAMPLE 3

N-cyclohexyl-2-(4'-pyridyl)propanamide [I, R=CH$_3$, A=>C=O, B=—NH, n=4]

To a stirred solution of lithium diisopropylamide (7.6 mmole) in anhydrous tetrahydrofuran (10 ml) is added N-cyclohexyl-4-pyridylacetamide (750 mg, 3.45 mmole) dissolved in anhydrous tetrahydrofuran (25 ml) dropwise at −70° C. under N$_2$. After 1 hr. of additional stirring at −70° C., there is added methyl iodide (0.24 ml, 3.8 mmole) dissolved in anhydrous tetrahydrofuran (3 ml). The reaction mixture is stirred at −70° C. for 30 min., then it is allowed to reach room temperature naturally. The solvent is evaporated in vacuo and the residue is partitioned between water (25 ml) and ethyl acetate (50 ml). The organic phase in separated and the aqueous phase in extracted with ethyl acetate (2×25 ml). The combined organic extracts (100 ml) are washed with water, brine, dried over sodium sulfate and evaporated in vacuo. The resulting is purified by flash column chromatography on silica gel eluting with chloroform:ethanol 95:5. There are obtained 550 mg (69% yield) of the title compound as a yellow solid, m.p. 125°–6° C.

Elemental analysis: Calculated % (found %): C 72.37 (72.16), H 8.68 (8.74), N 12.06 (11.93).

NMR (CDCl$_3$, δ): 1.50 (3H, d), 3.45 (1H, q), 3.75 (1H, m), 5.20 (1H, br s), 7.25 (2H, dd), 8,57 (2H, dd).

IR (CHCl$_3$, cm$^{-1}$): 3430, 3320, 3070, 3020, 2920, 2840, 1660, 1595, 1505.

In analogous fashion and starting from the appropriate precursors of formula (II) the following compounds may be prepared:
N-cyclohexyl-2-(4'-pyridyl)butanamide;
N-cyclohexyl-2-(4'-pyridyl)pentanamide;
N-cyclopropyl-2-(4'-pyridyl)propanamide;
Cyclohexyl 2-(4'-pyridyl)propionate;
Cyclohexyl 2-(4'-pyridyl)butanoate;
Cyclohexyl 2-(4'-pyridyl)pentanoate;
Cyclopentyl 2-(4'-pyridyl)propionate;
Cyclopropyl 2-(4'-pyridyl)propionate;
1-Cyclohexyl-3-(4'-pyridyl)-2-butanone;
1-Cyclohexyl-3-(4'-pyridyl)-2-pentanone;
1-Cyclohexyl-3-(4'-pyridyl)-2-hexanone;
1-Cyclopentyl-3-(4'-pyridyl)-2-butanone; and
1-Cyclopropyl-3-(4'-pyridyl)-2-butanone.

EXAMPLE 4

N-[1-(4'-pyridyl)ethyl]cyclohexanecarboxyamide (I, R=CH$_3$, A=—NH—, B=>C=O, n=4)

To a stirred suspension of cyclohexanecarboxylic acid (1.43 g, 15 mmole) in dry benzene (40 ml) is added thionyl chloride (6.0 ml). The resulting mixture is refluxed for 4 hours, cooled and evaporated in vacuo to yield a brown oil. The acyl chloride so obtained, dissolved in dry benzene (15 ml), is then added dropwise to a stirred solution of 1-(4'-pyridyl)ethylamine (1.83 g, 15 mmole) and triethylamine (4.2 ml, 30 mmole) in dry benzene (50 ml) at 5°–10° C.

After 3 hours of additional stirring at room temperature, the reaction mixture is worked up as described in the Example 1. There are obtained 1.74 g (50% yield) of the title compound.

Elemental analysis: Calculated % (found %): C 72.37 (72.21), H 8.68 (8.80), N 12.06 (11.83).

IR (CHCl$_3$, cm$^{-1}$): 3430, 1660, 1590, 1505.

In analogous fashion and starting from the appropriate precursors of formula (III) and (IV) the following compounds may be prepared:
N-[1-(4'-pyridyl)ethyl]cyclopentanecarboxyamide;
N-[1-(4'-pyridyl)ethyl]cyclopropanecarboxyamide;
1-(4'-pyridyl)ethyl cyclohexanecarboxylate;
1-(4'-pyridyl)ethyl cyclopentanecarboxylate;
1-(4'-pyridyl)ethyl cyclopropanecarboxylate;
2-(4'-pyridyl)propylcyclohexyl ketone;
2-(4'-pyridyl)propylcyclopentyl ketone; and
2-(4'-pyridyl)propylcyclopropyl ketone.

EXAMPLE 5

N-cyclohexyl-2-(4'-pyridyl)propylamine bis hydrochloride [I, R=CH$_3$, A=—CH$_2$—, B=—NH—, n=4]

To a stirred suspension of lithium aluminum hydride (0.4 g) in anydrous diglyme (10 ml) is added N-cyclohexyl 2-(4'-pyridyl)propanamide (0.464 g, 2 mmole), prepared as described in the Example 3, dissolved in anhydrous diglyme (5 ml) dropwise and under nitrogen atmosphere.

The reaction mixture is then heated at 85°–95° C. for 6 hrs. After cooling, the excess of lithium aluminium hydride is decomposed by the careful addition of a mixture of methanol, t-butylmethylether and water. The organic phase is separated, washed with water, dried over Na$_2$SO$_4$ and filtered. The filtrate is saturated with anhydrous hydrogen chloride and the resulting precipitate is filtered off and recrystallized from methanol:isopropanol 1:2. There are obtained 0.48 g (82% yield) of the title compound as bis hydrochloride.

Elemental analysis: calculated % (foud %): C 57.73 (57.81), H 8.24 (8.19), N 9.62 (9.55), Cl 24.05 (23.91).

IR (KBr, cm$^{-1}$): 3100–2300, 2840, 1595, 1505.

In analogus fashion the bis hydrochloride of the following compounds may be prepared:
N-cyclohexyl-2-(4'-pyridyl)butylamine;
N-cyclohexyl-2-(4'-pyridyl)pentylamine;
N-cyclopentyl-2-(4'-pyridyl)propylamine;
N-cyclopropyl-2-(4'-pyridyl)propylamine
N-cyclohexylmethyl-1-(4'-pyridyl)ethylamine;
N-cyclopentylmethyl-1-(4'-pyridyl)ethylamine;
N-cyclopropylmethyl-1-(4'-pyridyl)ethylamine, and
N-[1-(4'-pyridyl)ethyl]cyclohexylmethylamine.

EXAMPLE 6

2-(4'-pyridyl)propylcyclohexyl ether [I, R=CH$_3$, A=—CH$_2$—, B=—O—, n=4]

To a stirred suspension of lithium aluminum hydride (2.5 g) in anhydrous tetrahydrofuran (50 ml) is added a mixture of cyclohexyl 2-(4'-pyridyl)propionate (3.50 g, 15 mmole), prepared as described in the Example 3, and borontrifluoride etherate (30 ml) in anhydrous tetrahydrofuran (50 ml) dropwise with external cooling. After 3 hrs. at 45° C. the reaction mixture is carefully decomposed by adding water, followed by a 23% hydrochloric acid solution. Most of the organic solvent is evaporated in vacuo, the aqueous solution is brought to pH 9 by adding a concentrated sodium hydroxyde solution and extracted with diethyl ether (3 times). The combined extracts are washed with water to neutral, dried over Na$_2$SO$_4$ and evaporated in vacuo. The resulting residue is purified by column chromatography on silica gel eluting with benzene:ethyl acetate 95:5 and by fractional distillation. There are obtained 2.2 g (65% yield) of the title compound, Elemental analysis: calculated % (found %): C 76.71 (76.82), H 9.58 (9.62), N 6.39 (6.31).

IR (CHCl$_3$, cm$^{-1}$): 1585, 1505, 1175, 1130.

In analogous fashion the following compounds may be prepared:
2-(4'-pyridyl)butylcyclohexyl ether;
2-(4'-pyridyl)pentylcyclohexyl ether;
2-(4'-pyridyl)propylcyclopentyl ether;
2-(4'-pyridyl)propylcyclopropyl ether;
1-(4'-pyridyl)ethyl(cyclohexylmethyl)ether;
1-(4'-pyridyl)ethyl(cyclopentylmethyl)ether; and
1-(4'-pyridyl)ethyl(cyclopropylmethyl)ether.

EXAMPLE 7

1-cyclohexyl-3-(4'-pyridyl)butane [I, R=CH$_3$, A=B=—CH$_2$—, n=4]

To a solution of 1-cyclohexyl-3-(4'-pyridyl)-2-butanone (2.31 g, 10 mmole), prepared as described in the Example 3, in methylene chloride (50 ml) are added ethanedithiol (2 ml) and boron trifluoride etherate (2 ml). The mixture is stirred at room temperature during 2 hours, then it is washed with water, a 8% NaHCO$_3$ aqueous solution and water, then dried over CaCl$_2$, filtered and evaporated in vacuo. The crude thioketal so obtained (3.1 g) is dissolved in anhydrous tetrahydrofuran (30 ml) and stirred in presence of Raney nickel (10 g) (prepared according to Org. Synth., 3, 181)—for 2 hours at room temperature. The catalyst is filtered off and washed with methylene chloride.

The combined filtrate and washings are evaporated in vacuo to yield a residue which is purified by fractional distillation.

There are obtained 1.3 g (60% yield) of the title compound.

Elemental analysis: calculated % (found %) C 82.94 (82.88), H 10.59 (10.61), N 6.45 (6.44).

In analogus fashion the following compounds may be prepared:

1-cyclohexyl-3-(4'-pyridyl)pentane;
1-cyclohexyl-3-(4'-pyridyl)hexane;
1-cyclopentyl-3-(4'-pyridyl)butane; and
1-cyclopropyl-3-(4'-pyridyl)butane.

EXAMPLE 8

N-cyclohexyl-(2'-methylpyrid-4'-yl)acetamide [II, R$_1$=2'—CH$_3$, R$_2$=H, B=NH, n=4]

To a stirred suspension of 2-methylpyrid-4-yl acetic acid hydrochloride (1.87 g, 10 mmole) in anhydrous tetrahydrofuran (10 ml), is added N,N'-carbonyldiimidazole (1.62 g, 10 mmole) at 25° C. After 2 hrs of additional stirring there is added cyclohexylamine (1.15 ml, 10 mmole) dissolved in tetrahydrofuran (15 ml) dropwise. The reaction mixture is stirred overnight, the solvent is evaporated in vacuo and the residue in taken up with water (25 ml) and ethyl acetate (50 ml).

The pH is adjusted by the addition of 1N NaOH aqueous solution (11 ml), the organic phase is separated and the aqueous phase extracted with ethyl acetate (2×50 ml).

The combined extracts (150 ml) are washed with water, brine, dried over sodium sulfate, filtered and evaporated in vacuo. The resulting residue is purified by crystallisation from hot water (50 ml) at 5°-10° C.

There are obtained 580 mg (25% yield) of the title compound,

Elemental analysis: calculated % (found %) C 72.37 (72.10), H 8.68 (8.77), N 12.06 (11.97).

IR (CHCl$_3$, cm$^{-1}$): 3420, 1660, 1600, 1555.

In analogous fashion, starting from the appropriate precursors of formula (V) and of formula (VI) or, respectively, of formula (VII) the following compounds can be prepared:

N-cyclohexyl-(3'-methylpyrid-4'-yl)acetamide;
N-cyclohexyl-(2',6'-dimethylpyrid-4'-yl)acetamide;
N-cyclohexyl-(2',5'-dimethylpyrid-4'-yl)acetamide;
N-cyclohexyl-(2',3'-dimethylpyrid-4'-yl)acetamide;
N-cyclohexyl-(3',5'-dimethylpyrid-4'-yl)acetamide;
N-cyclopentyl-(2'-methylpyrid-4'-yl)acetamide;
N-cyclopentyl-(3'-methylpyrid-4'-yl)acetamide;
N-cyclopentyl-(2',6'-dimethylpyrid-4'-yl)acetamide;
N-cyclopentyl-(2',5'-dimethylpyrid-4'-yl)acetamide;
N-cyclopentyl-(2',3'-dimethylpyrid-4'-yl)acetamide;
N-cyclopentyl-(3',5'-dimethylpyrid-4'-yl)acetamide;
cyclohexyl(2'-methylpyrid-4'-yl)acetate;
cyclohexyl(3'-methylpyrid-4'-yl)acetate;
cyclohexyl(2',6'-dimethylpyrid-4'-yl)acetate;
cyclohexyl(2',5'-dimethylpyrid-4'-yl)acetate;
cyclohexyl(2',3'-dimethylpyrid-4'-yl)acetate; and
cyclohexyl(3',5'-dimethylpyrid-4'-yl)acetate.

EXAMPLE 9

1-cyclohexyl-3-(2'-methylpyrid-4'-yl)-2-propanone [II, R$_1$=2'—CH$_3$, R$_2$=H, B=CH$_2$, n=4]

To a stirred solution of cyclohexyl methyl magnesium bromide (prepared from 1.77 g of cyclohexyl methyl bromide and 0.250 g of magnesium turnings) in anhydrous tetrahydrofuran (30 ml) cooled to −70° C. are added 10 mmole of the imidazoyl derivatives of 2-methylpyrid-4-yl acetic acid (prepared as described in the Example 8). After 4 hours of additional stirring at that temperature, the reaction mixture is allowed to reach room temperature naturally and it is carefully decomposed by the dropwise addition of a saturated ammonium chloride aqueous solution. The organic phase is separated and the aqueous phase is extracted with diethyl ether (2×50 ml). The combined extracts are washed with brine, dried over sodium sulfate, filtered and evaporated in vacuo. The resulting residue is purified by fractional distillation. There are obtained 0.81 g (35% yield) of the title compound.

IR (CHCl$_3$, cm$^{-1}$): 1715, 1595, 1545

In analogous fashion the following compounds can be prepared:

1-cyclohexyl-3-(3'-methylpyrid-4'-yl)-2-propanone;
1-cyclohexyl-3-(2',6'-dimethylpyrid-4'-yl)-2-propanone;
1-cyclohexyl-3-(2',5'-dimethylpyrid-4'-yl)-2-propanone;
1-cyclohexyl-3-(2',3'-dimethylpyrid-4'-yl)-2-propanone; and
1-cyclohexyl-3-(3',5'-dimethylpyrid-4'-yl)-2-propanone.

EXAMPLE 10

N-cyclohexyl-2-(2'-methylpyrid-4'-yl)propanamide [I, R=CH$_3$, R$_1$=2'—CH$_3$, R$_2$=H, A=>C=O, B=—NH—, n=4]

To a stirred solution of lithium diisopropylamide (7.6 mmole) in anhydrous tetrahydrofuran (10 ml) is added N-cyclohexyl(2'-methylpyrid-4'-yl)acetamide (800 mg, 3.45 mmole) dissolved in anhydrous tetrahydrofuran (25 ml) dropwise at −70° C. under N$_2$. After 1 hr. of additional stirring at −70° C., there is added methyl iodide (0.24 ml, 3.8 mmole) dissolved in anhydrous tetrahydrofuran (3 ml). The reaction mixture is stirred at −70° C. for 30 min., then it is allowed to reach room temperature naturally. The solvent is evaporated in vacuo and the residue is partitioned between water (25 ml) and ethyl acetate (50 ml). The organic phase in separated and the aqueous phase in extracted with ethyl acetate (2×25 ml). The combined organic extracts (100 ml) are washed with water, brine, dried over sodium sulfate and evaporated in vacuo. The resulting residue is purified by flash column chromatography on silica gel eluting with chloroform:ethanol 95:5. There are obtained 640 mg (75% yield) of the title compound as a yellow solid, Elemental analysis: Calculated % (found %): C 73.13 (73.27), H 9.00 (9.08), N 11.37 (11.23).

IR (CHCl$_3$, cm$^{-1}$): 3430, 3320, 3070, 3020, 2920, 2840, 1660, 1595, 1505.

In analogous fashion and starting from the appropriate precursors of formula (II) the following compounds may be prepared:

N-cyclohexyl-2-(3'-methylpyrid-4'-yl)propanamide;
N-cyclohexyl-2-(2',6'-dimethylpyrid-4'-yl)propanamide;
N-cyclohexyl-2-(2',5'-dimethylpyrid-4'-yl)propanamide;
N-cyclohexyl-2-(2',3'-dimethylpyrid-4'-yl)propanamide;
N-cyclohexyl-2-(3',5'-dimethylpyrid-4'-yl)propanamide;
cyclohexyl 2-(2'-methylpyrid-4'-yl)propionate;
cyclohexyl 2-(3'-methylpyrid-4'-yl)propionate;
cyclohexyl 2-(2',6'-dimethylpyrid-4'-yl)propionate;
cyclohexyl 2-(2',5'-dimethylpyrid-4'-yl)propionate;
cyclohexyl 2-(2',3'-dimethylpyrid-4'-yl)propionate;
cyclohexyl 2-(3',5'-dimethylpyrid-4'-yl)propionate;
1-cyclohexyl-3-(2'-methylpyrid-4'-yl)-2-butanone;
1-cyclohexyl-3-(3'-methylpyrid-4'-yl)-2-butanone;
1-cyclohexyl-3-(2',6'-dimethylpyrid-4'-yl)-2-butanone;
1-cyclohexyl-3-(2',5'-dimethylpyrid-4'-yl)-2-butanone;
1-cyclohexyl-3-(2',3'-dimethylpyrid-4'-yl)-2-butanone;
1-cyclohexyl-3-(3',5'-dimethylpyrid-4'-yl)-2-butanone;
N-cyclopentyl-2-(2'-methylpyrid-4'-yl)propanamide;
N-cyclopentyl-2-(3'-methylpyrid-4'-yl)propanamide;
N-cyclopentyl-2-(2',6'-dimethylpyrid-4'-yl)propanamide;
N-cyclopentyl-2-(2',5'-dimethylpyrid-4'-yl)propanamide;
N-cyclopentyl-2-(2',3'-dimethylpyrid-4'-yl)propanamide; and
N-cyclopentyl-2-(3',5'-dimethylpyrid-4'-yl)propanamide.

EXAMPLE 11

N-[1-(2'-methylpyrid-4'-yl)ethyl]cyclohexanecarboxamide [I, R=CH$_3$, R$_1$=2'—CH$_3$, R$_2$=H, A=NH—, B=>C=O, n=4]

To a stirred suspension of cyclohexanecarboxylic acid (1.92 g, 15 mmole) in dry benzene (40 ml) is added thionyl chloride (2.0 ml). The resulting mixture is refluxed for 4 hours, cooled and evaporated in vacuo to yield a brown oil. The acyl chloride so obtained, dissolved in dry benzene (15 ml), is then added dropwise to a stirred solution of 1-(2'-methylpyrid-4'-yl)ethylamine (2.04 g, 15 mmole) and triethylamine (4.2 ml, 30 mmole) in dry benzene (50 ml) at 5°–10° C.

After 3 hours of additional stirring at room temperature, the reaction mixture is worked up as described in the Example 8. There are obtained 2.21 g (60% yield) of the title compound.

Elemental analysis: Calculated % (found %): C 73.13 (73.28), H 9.00 (8.91), N 11.37 (11.25).

IR (CHCl$_3$, cm$^{-1}$): 3430, 1660, 1590, 1505.

In analogous fashion, starting from the appropriate precursors of formula (III) and (IV), the following compounds may be prepared:

N-[1-(3'-methylpyrid-4'-yl)ethyl]cyclohexanecarboxamide;
N-[1-(2',6'-dimethylpyrid-4'-yl)ethyl]cyclohexanecarboxamide;
N-[1-(2',5'-dimethylpyrid-4'-yl)ethyl]cyclohexanecarboxamide;
N-[1-(2',3'-dimethylpyrid-4'-yl)ethyl]cyclohexanecarboxamide;
N-[1-(3',5'-dimethylpyrid-4'-yl)ethyl]cyclohexanecarboxamide;
1-(2'-methylpyrid-4'-yl)ethyl cyclohexanecarboxylate;
1-(3'-methylpyrid-4'-yl)ethyl cyclohexanecarboxylate;
1-(2',6'-dimethylpyrid-4'-yl)ethyl cyclohexanecarboxylate;
1-(2',5'-dimethylpyrid-4'-yl)ethyl cyclohexanecarboxylate;
1-(2',3'-dimethylpyrid-4'-yl)ethyl cyclohexanecarboxylate;
1-(3',5'-dimethylpyrid-4'-yl)ethyl cyclohexanecarboxylate;
2-(2'-methylpyrid-4'-yl)propylcyclohexylketone;
2-(3'-methylpyrid-4'-yl)propylcyclohexylketone;
2-(2',6'-dimethylpyrid-4'-yl)propylcyclohexylketone;
2-(2',5'-dimethylpyrid-4'-yl)propylcyclohexylketone;
2-(2',3'-dimethylpyrid-4'-yl)propylcyclohexylketone; and
2-(3',5'-dimethylpyrid-4'-yl)propylcyclohexylketone.

EXAMPLE 12

N-cyclohexyl-2-(2'-methylpyrid-4-yl)propylamine bis hydrochloride [I, R=CH$_3$, R$_1$=2'—CH$_3$, R$_2$=H, A=—CH$_2$—, B=—NH—, n=4]

To a stirred suspension of lithium aluminum hydride (0.4 g) in anydrous diglyme (10 ml) is added N-cyclohexyl 2-(2'-methylpyrid-4'-yl)propanamide (0.492 g, 2 mmole), prepared as described in the Example 10, dissolved in anhydrous diglyme (5 ml) dropwise and under nitrogen atmosphere.

The reaction mixture is then heated at 85°–95° C. for 6 hrs. After cooling, the excess of lithium aluminium hydride is decomposed by the careful addition of a mixture of methanol, t-butylmethylether and water. The organic phase is separated, washed with water, dried over Na$_2$SO$_4$ and filtered. The filtrate is saturated with anhydrous hydrogen chloride and the resulting precipitate is filtered off and recrystallized from methanol:isopropanol 1:2. There are obtained 0.450 g (74% yield) of the title compound as bis hydrochloride.

Elemental analysis: calculated % (foud %): C 59.01 (59.25), H 8.58 (8.65); N 9.18 (9.07), 23.23 (23.02).

IR (KBr, cm$^{-1}$): 3100–2300, 2840, 1595, 1505.

In analogus fashion the bis hydrochloride of the following compounds may be prepared:

N-cyclohexyl-2-(3'-methylpyrid-4'-yl)propylamine;
N-cyclohexyl-2-(2',6'-dimethylpyrid-4'-yl)propylamine;
N-cyclohexyl-2-(2',5'-dimethylpyrid-4'-yl)propylamine;
N-cyclohexyl-2-(2',3'-dimethylpyrid-4'-yl)propylamine;
N-cyclohexyl-2-(3',5'-dimethylpyrid-4'-yl)propylamine;
N-[1-(2'-methylpyrid-4'-yl)ethyl]cyclohexylmethylamine;
N-[1-(3'-methylpyrid-4'-yl)ethyl]cyclohexylmethylamine;
N-[1-(2',6'-dimethylpyrid-4'-yl)ethyl]cyclohexylmethylamine;
N-[1-(2',5'-dimethylpyrid-4'-yl)ethyl]cyclohexylmethylamine;
N-[1-(2',3'-dimethylpyrid-4'-yl)ethyl]cyclohexylmethylamine; and
N-[1-(3',5'-dimethylpyrid-4'-yl)ethyl]cyclohexylmethylamine.

EXAMPLE 13

2-(2'-methylpyrid-4'-yl)propylcyclohexyl ether [I, R=CH$_3$, R$_1$=2'—CH$_3$, R$_2$=H, A=—CH$_2$—, B=—O—, n=4]

To a stirred suspension of lithium aluminum hydride (2.5 g) in anhydrous tetrahydrofuran (50 ml) is added a mixture of cyclohexyl 2-(2'-methylpyrid-4'-yl)propionate (3.70 g, 15 mmole), prepared as described in the Example 10, and borontrifluoride etherate (30 ml) in anhydrous tetrahydrofuran (50 ml) dropwise with external cooling. After 3 hrs. at 45° C. the reaction mixture is carefully decomposed by adding water, followed by a 23% hydrochloric acid solution. Most of the organic solvent is evaporated in vacuo, the aqueous solution is brought to pH 9 by adding a concentrated sodium hydroxyde solution and extracted with diethyl ether (3 times). The combined extracts are washed with water to neutral, dried over Na$_2$SO$_4$ and evaporated in vacuo. The resulting residue is purified by column chromatography on silica gel eluting with benzene:ethyl acetate 95:5 and by fractional distillation. There are obtained 2.25 g (65% yield) of the title compound, Elemental analysis: calculated % (found %): C 77.20 (77.35), H 9.94 (9.85), N 6.00 (5.91).

IR (CHCl$_3$, cm$^{-1}$): 1585, 1505, 1175, 1130.

In analogous fashion the following compounds may be prepared;
2-(3'-methylpyrid-4'-yl)propylcyclohexyl ether;
2-(2',6'-dimethylpyrid-4'-yl)propylcyclohexyl ether;
2-(2',5'-dimethylpyrid-4'-yl)propylcyclohexyl ether;
2-(2',3'-dimethylpyrid-4'-yl)propylcyclohexyl ether;
2-(3',5'-dimethylpyrid-4'-yl)propylcyclohexyl ether;
1-(2'-methylpyrid-4'-yl)ethyl cyclohexylmethyl ether;
1-(3'-methylpyrid-4'-yl)ethyl cyclohexylmethyl ether;
1-(2',6'-dimethylpyrid-4'-yl)ethyl cyclohexylmethyl ether;
1-(2',5'-dimethylpyrid-4'-yl)ethyl cyclohexylmethyl ether;
1-(2',3'-dimethylpyrid-4'-yl)ethyl cyclohexylmethyl ether; and
1-(3',5'-dimethylpyrid-4'-yl)ethyl cyclohexylmethyl ether.

EXAMPLE 14

1-cyclohexyl-3-(2'-methylpyrid-4'-yl)butane [I, R=CH$_3$, R$_1$=2'—CH$_3$, R$_2$=H, A=B=—CH$_2$—, n=4]

To a solution of 1-cyclohexyl-3-(2'-methylpyrid-4'-yl)-2-butanone (2.45 g, 10 mmole), prepared as described in the Example 10, in methylene chloride (50 ml) are added ethanedithiol (2 ml) and boron trifluoride etherate (2 ml). The mixture is stirred at room temperature during 2 hours, then it is washed with water, a 8% NaHCO$_3$ aqueous solution and water, then dried over CaCl$_2$, filtered and evaporated in vacuo. The crude thioketal so obtained (2.80 g) is dissolved in anhydrous tetrahydrofuran (30 ml) and stirred in presence of Raney nickel (10 g) (prepared according to Org. Synth., 3, 181)—for 2 hours at room temperature. The catalyst is filtered off and washed with methylene chloride.

The combined filtrate and washings are evaporated in vacuo to yield a residue which is purified by fractional distillation.

There are obtained 1.15 g (50% yield) of the title compound.

Elemental analysis: calculated % (found %) C 83.05 (83.38), H 10.89 (10.98), N 6.05 (5.85).

In analogous fashion the following compounds may be prepared:
1-cyclohexyl-3-(3'-methylpyrid-4'-yl)butane;
1-cyclohexyl-3-(2',6'-dimethylpyrid-4'-yl)butane;
1-cyclohexyl-3-(2',5'-dimethylpyrid-4'-yl)butane;
1-cyclohexyl-3-(2',3'-dimethylpyrid-4'-yl)butane; and
1-cyclohexyl-3-(3',5'-dimethylpyrid-4'-yl)butane.

EXAMPLE 15

Tablets, each weighing 0.150 g and containing 25 mg of the active substance, can be manufactured as follows:
Composition (for 10,000 tablets):
N-cyclohexyl-2-(4'-pyridyl)propanamide: 250 g
Lactose: 800 g
Corn starch: 415 g
Talc powder: 30 g
Magnesium stearate 5 g.

N-cyclohexyl-2-(4'-pyridyl)propanamide, the lactose and half the corn starch are mixed; the mixture is then forced through a sieve of 0.5 mm mesh size.

Corn starch (10 g) is suspended in warm water (90 ml) and the resulting paste is used to granulate the powder.

The granulate is dried, comminuted on a sieve of 1.4 mm mesh size, then the remaining quantity of starch, talc and magnesium stearate is added, carefully mixed and processed into tablets.

We claim:

1. A cycloalkyl-substituted 4-pyridyl derivative of formula (I)

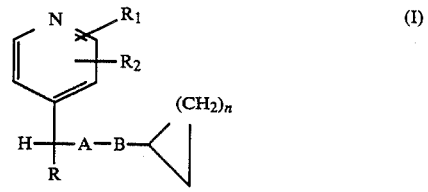

wherein
R is C$_1$–C$_4$ alkyl;
each of R$_1$ and R$_2$ is, independently, hydrogen or C$_1$–C$_4$ alkyl;
n is an integer of 1 to 5; and either
(a) A is >C=O and B is —O—, —NH— or —CH$_2$—; or
(b) A is —CH$_2$— and B is —O—, —NH—, —CH$_2$— or >C=O; or
(c) A is —O— and B is >C=O or —CH$_2$—; or
(d) A is —NH— and B is >C=O or —CH$_2$—,
and the pharmaceutically acceptable salts thereof.

2. A cycloalkyl substituted 4-pyridyl derivative of formula (I) according to claim 1 wherein R is C$_1$–C$_4$ alkyl;
each of R$_1$ and R$_2$ is, independently, hydrogen or C$_1$–C$_4$ alkyl;
n is an integer of 1 to 5;
A is >C=O or —CH$_2$— and B is, independently, —O—, —NH— or —CH$_2$—,
and the pharmaceutically acceptable salt thereof.

3. A compound according to claim 1 or 2, wherein the derivative of formula (I) is an enantiomer of formula (Ia)

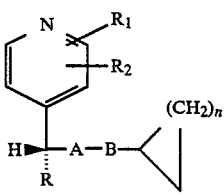

wherein
R, R₁, R₂, n, A and B are as defined in claim 1 or 2.

4. A compound according to claim 1 or 2 wherein either $R_1$ and $R_2$ are both hydrogen or both methyl groups, or one of them is hydrogen and the other is methyl, and n is 3 or 4.

5. A compound, either as single enantiomer or as racemic mixture, selected from the group consisting of:
cyclohexyl 2-(4'-pyridyl)propionate;
cyclohexyl 2-(2'-methylpyrid-4'-yl)propionate;
cyclohexyl 2-(3-methylpyrid-4'-yl)propionate;
cyclohexyl 2-(2',6'-dimethylpyrid-4'-yl)propionate;
cyclohexyl 2-(2',5'-dimethylpyrid-4'-yl)propionate;
cyclohexyl 2-(2',3'-dimethylpyrid-4'-yl)propionate;
cyclohexyl 2-(3',5'-dimethylpyrid-4'-yl)propionate;
N-cyclohexyl-2-(4'-pyridyl)propanamide;
N-cyclohexyl-2-(2'-methylpyrid-4'-yl)propanamide;
N-cyclohexyl-2-(3'-methylpyrid-4'-yl)propanamide;
N-cyclohexyl-2-(2',6'-dimethylpyrid-4'-yl)propanamide;
N-cyclohexyl-2-(2',5'-dimethylpyrid-4'-yl)propanamide;
N-cyclohexyl-2-(2',3'-dimethylpyrid-4'-yl)propanamide;
N-cyclohexyl-2-(3',5'-dimethylpyrid-4'-yl)propanamide;
2-(4'-pyridyl)propylcyclohexyl ether;
2-(2'-methylpyrid-4'-yl)propylcyclohexyl ether;
2-(3'-methylpyrid-4'-yl)propylcyclohexyl ether;
2-(2',6'-dimethylpyrid-4'-yl)propylcyclohexyl ether;
2-(2',5'-dimethylpyrid-4'-yl)propylcyclohexyl ether;
2-(2',3'-dimethylpyrid-4'-yl)propylcyclohexyl ether;
2-(3',5'-dimethylpyrid-4'-yl)propylcyclohexyl ether;
N-cyclohexyl-2-(4'-pyridyl)propylamine;
N-cyclohexyl-2-(2'-methylpyrid-4'-yl)propylamine;
N-cyclohexyl-2-(3'-methylpyrid-4-yl)propylamine;
N-cyclohexyl-2-(2',6'-dimethylpyrid-4'-yl)propylamine;
N-cyclohexyl-2-(2',5'-dimethylpyrid-4'-yl)propylamine;
N-cyclohexyl-2-(2',3'-dimethylpyrid-4'-yl)propylamine;
N-cyclohexyl-2-(3',5'-dimethylpyrid-4'-yl)propylamine;
1-cyclohexyl-3-(4'-pyridyl)-2-butanone;
1-cyclohexyl-3-(2'-methylpyrid-4'-yl)-2-butanone;
1-cyclohexyl-3-(3'-methylpyrid-4'-yl)-2-butanone;
1-cyclohexyl-3-(2',6'-dimethylpyrid-4'-yl)-2-butanone;
1-cyclohexyl-3-(2',5'-dimethylpyrid-4'-yl)-2-butanone;
1-cyclohexyl-3-(2',3'-dimethylpyrid-4'-yl)-2-butanone;
1-cyclohexyl-3-(3',5'-dimethylpyrid-4'-yl)-2-butanone;
1-cyclohexyl-3-(4'-pyridyl)butane;
1-cyclohexyl-3-(2'-methylpyrid-4'-yl)butane;
1-cyclohexyl-3-(3'-methylpyrid-4'-yl)butane;
1-cyclohexyl-3-(2',6'-dimethylpyrid-4'-yl)butane;
1-cyclohexyl-3-(2',5'-dimethylpyrid-4'-yl)butane;
1-cyclohexyl-3-(2',3'-dimethylpyrid-4'-yl)butane;
1-cyclohexyl-3-(3',5'-dimethylpyrid-4'-yl)butane;
1-(4'-pyridyl)ethyl cyclohexanecarboxylate;
1-(2'-methylpyrid-4'-yl)ethyl cyclohexanecarboxylate;
1-(3'-methylpyrid-4'-yl)ethyl cyclohexanecarboxylate;
1-(2',6'-dimethylpyrid-4'-yl)ethyl cyclohexanecarboxylate;
1-(2',5'-dimethylpyrid-4'-yl)ethyl cyclohexanecarboxylate;
1-(2',3'-dimethylpyrid-4'-yl)ethyl cyclohexanecarboxylate;
1-(3',5'-dimethylpyrid-4'-yl)ethyl cyclohexanecarboxylate;
1-(4'-pyridyl)ethyl cyclohexylmethyl ether;
1-(2'-methylpyrid-4'-yl)ethyl cyclohexylmethyl ether;
1-(3'-methylpyrid-4'-yl)ethyl cyclohexylmethyl ether;
1-(2',6'-dimethylpyrid-4'-yl)ethyl cyclohexylmethyl ether;
1-(2',5'-dimethylpyrid-4'-yl)ethyl cyclohexylmethyl ether;
1-(2',3'-dimethylpyrid-4'-yl)ethyl cyclohexylmethyl ether;
1-(3',5'-dimethylpyrid-4'-yl)ethyl cyclohexylmethyl ether;
N-[1-(4'-pyridyl)ethyl]cyclohexanecarboxyamide;
N-[1-(2'-methylpyrid-4'-yl)ethyl]cyclohexanecarboxyamide;
N-[1-(3'-methylpyrid-4'-yl)ethyl]cyclohexanecarboxyamide;
N-[1-(2',6'-dimethylpyrid-4'-yl)ethyl]cyclohexanecarboxyamide;
N-[1-(2',5'-dimethylpyrid-4'-yl)ethyl]cyclohexanecarboxyamide;
N-[1-(2',3'-dimethylpyrid-4'-yl)ethyl]cyclohexanecarboxyamide;
N-[1-(3',5'-dimethylpyrid-4'-yl)ethyl]cyclohexanecarboxyamide;
N-[1-(4'-pyridyl)ethyl]cyclohexylmethylamine;
N-[1-(2'-methylpyrid-4'-yl)ethyl]cyclohexylmethylamine;
N-[1-(3'-methylpyrid-4'-yl)ethyl]cyclohexylmethylamine;
N-[1-(2',6'-dimethylpyrid-4'-yl)ethyl]cyclohexylmethylamine;
N-[1-(2',5'-dimethylpyrid-4'-yl)ethyl]cyclohexylmethylamine;
N-[1-(2',3'-dimethylpyrid-4'-yl)ethyl]cyclohexylmethylamine;
N-[1-(3',5'-dimethylpyrid-4'-yl)ethyl]cyclohexylmethylamine;
2-(4'-pyridyl)propylcyclohexylketone;
2-(2'-methylpyrid-4'-yl)propylcyclohexylketone;
2-(3'-methylpyrid-4'-yl)propylcyclohexylketone;
2-(2',6'-dimethylpyrid-4'-yl)propylcyclohexylketone;
2-(2',5'-dimethylpyrid-4'-yl)propylcyclohexylketone;
2-(2',3'-dimethylpyrid-4'-yl)propylcyclohexylketone;
2-(3',5'-dimethylpyrid-4'-yl)propylcyclohexylketone;
and the pharmaceutically acceptable salts thereof.

6. A compound, either as single enantiomer or as racemic mixture, selcted from the group consisting of:
cyclohexyl 2-(4'-pyridyl)propionate;
cyclohexyl 2-(2'-methylpyrid-4'-yl)propionate;
cyclohexyl 2-(3'-methylpyrid-4'-yl)propionate;
cyclohexyl 2-(2',6'-dimethylpyrid-4'-yl)propionate;
cyclohexyl 2-(2',5'-dimethylpyrid-4'-yl)propionate;
cyclohexyl 2-(2',3'-dimethylpyrid-4'-yl)propionate;
cyclohexyl 2-(3',5'-dimethylpyrid-4'-yl)propionate;
N-cycohexyl-2-(4'-pyridyl)propanamide;
N-cyclohexyl-2-(2'-methylpyrid-4'-yl)propanamide;
N-cyclohexyl-2-(3'-methylpyrid-4'-yl)propanamide;
N-cyclohexyl-2-(2',6'-dimethylpyrid-4'-yl)propanamide;

N-cyclohexyl-2-(2',5'-dimethylpyrid-4'-yl)propanamide;
N-cyclohexyl-2-(2',3'-dimethylpyrid-4'-yl)propanamide;
N-cyclohexyl-2-(3',5'-dimethylpyrid-4'-yl)propanamide;
2-(4'-pyridyl)propylcyclohexyl ether;
2-(2'-methylpyrid-4'-yl)propylcyclohexyl ether;
2-(3'-methylpyrid-4'-yl)propylcyclohexyl ether;
2-(2',6'-dimethylpyrid-4'-yl)propylcyclohexyl ether;
2-(2',5'-dimethylpyrid-4'-yl)propylcyclohexyl ether;
2-(2',3'-dimethylpyrid-4'-yl)propylcyclohexyl ether;
2-(3',5'-dimethylpyrid-4'-yl)propylcyclohexyl ether;
N-cyclohexyl-2-(4'-pyridyl)propylamine;
N-cyclohexyl-2-(2'-methylpyrid-4'-yl)propylamine;
N-cyclohexyl-2-(3'-methylpyrid-4'-yl)propylamine;
N-cyclohexyl-2-(2',6'-dimethylpyrid-4'-yl)propylamine;
N-cyclohexyl-2-(2',5'-dimethylpyrid-4'-yl)propylamine;
N-cyclohexyl-2-(2',3'-dimethylpyrid-4'-yl)propylamine;
N-cyclohexyl-2-(3',5'-dimethylpyrid-4'-yl)propylamine;
1-cyclohexyl-3-(4'-pyridyl)-2-butanone;
1-cyclohexyl-3-(2'-methylpyrid-4'-yl)-2-butanone;
1-cyclohexyl-3-(3'-methylpyrid-4'-yl)-2-butanone;
1-cyclohexyl-3-(2',6'-dimethylpyrid-4'-yl)-2-butanone;
1-cyclohexyl-3-(2',5'-dimethylpyrid-4'-yl)-2-butanone;
1-cyclohexyl-3-(2',3'-dimethylpyrid-4'-yl)-2-butanone;
1-cyclohexyl-3-(3',5'-dimethylpyrid-4'-yl)-2-butanone;
1-cyclohexyl-3-(4'-pyridyl)butane;
1-cyclohexyl-3-(2'-methylpyrid-4'-yl)butane;
1-cyclohexyl-3-(3'-methylpyrid-4'-yl)butane;
1-cyclohexyl-3-(2',6'-dimethylpyrid-4'-yl)butane;
1-cyclohexyl-3-(2',5'-dimethylpyrid-4'-yl)butane;
1-cyclohexyl-3-(2',3'-dimethylpyrid-4'-yl)butane;
1-cyclohexyl-3-(3',5'-dimethylpyrid-4'-yl)butane,
and the pharmaceutically acceptable salts thereof.

7. A salt of a compound of claim 5 or 6 wherein the salt is the hydrochloride.

8. A compound of claim 3, wherein either $R_1$ or $R_2$ are both hydrogen or both methyl groups, or one of them is hydrogen and the other is methyl, and n is 3 or 4.

9. A compound of claim 1, wherein said compound is N-cyclohexyl-2-(4'-pyridyl)propanamide.

10. A compound of claim 1, wherein said compound is 1-cyclohexyl-3-(4'-pyridyl)-2-butanone.

11. Method of producing inhibition of the enzyme aromatase in a patient in need of it, which method comprises administering to the patient an effective amount of a compound according to claim 1.

12. Method of producing inhibition of the enzyme aromatase in a patient in need of it, which method comprises administering to the patient an effective amount of a composition according to claim 9.

13. Method of treating estrogen-dependent tumors or prostatic hyperplasia in a patient in need of it, which method comprises administering to the patient an aromatase-inhibiting effective amount of a compound according to claim 1.

14. Method of treating estrogen-dependent tumors or prostatic hyperplasia in a patient in need of it, which method comprises administering to the patient an aromatase-inhibiting effective amount of a composition according to claim 9.

15. Method according to claim 13 wherein the estrogen-dependent tumor is a breast tumor or an ovarian tumor or an endometrial tumor or a pancreatic tumor.

16. Method according to claim 14 wherein the estrogen-dependent tumor is a breast tumor or an ovarian tumor or an endometrial tumor or a pancreatic tumor.

17. A pharmaceutical composition for inhibiting aromatase comprising an inert carrier and/or diluent and, as the active substance, an effective amount of a compound of formula (I) according to claim 1 or a pharmaceutically acceptable salt thereof.

* * * * *